United States Patent
Hidas

(10) Patent No.: US 12,232,873 B2
(45) Date of Patent: Feb. 25, 2025

(54) METHOD AND A SYSTEM FOR MEASURING INSTANTANEOUS INFLOW RATE OF URINE

(71) Applicant: Bright Uro, Inc., Irvine, CA (US)

(72) Inventor: Gil Hidas, Victoria (AU)

(73) Assignee: Bright Uro, Inc., Irvine, CA (US)

( * ) Notice: Subject to any disclaimer, the term of this patent is extended or adjusted under 35 U.S.C. 154(b) by 664 days.

(21) Appl. No.: 17/606,653

(22) PCT Filed: Apr. 28, 2020

(86) PCT No.: PCT/IB2020/053979
§ 371 (c)(1),
(2) Date: Oct. 26, 2021

(87) PCT Pub. No.: WO2020/222112
PCT Pub. Date: Nov. 5, 2020

(65) Prior Publication Data
US 2022/0192567 A1    Jun. 23, 2022

Related U.S. Application Data

(60) Provisional application No. 62/840,195, filed on Apr. 29, 2019.

(51) Int. Cl.
*A61B 5/20* (2006.01)
*A61B 5/00* (2006.01)
(Continued)

(52) U.S. Cl.
CPC ............ *A61B 5/208* (2013.01); *A61B 5/6887* (2013.01); *G01F 23/241* (2013.01);
(Continued)

(58) Field of Classification Search
CPC ......... A61B 5/202; A61B 5/208; A61B 5/207; A61B 10/007; A61B 2560/0223;
(Continued)

(56) References Cited

U.S. PATENT DOCUMENTS

| 3,241,368 A | 3/1966 | Newitt |
| 3,363,619 A | 1/1968 | Keitzer |

(Continued)

FOREIGN PATENT DOCUMENTS

| AU | 2005291472 B2 | 2/2012 |
| CN | 106073808 A | 11/2016 |

(Continued)

OTHER PUBLICATIONS

Fukahori JP 09248289 A, translation from Espacenet (Year: 1997).*
(Continued)

*Primary Examiner* — Daniel L Cerioni
*Assistant Examiner* — Abel Seifu Abegaz
(74) *Attorney, Agent, or Firm* — Knobbe, Martens, Olson & Bear, LLP

(57) ABSTRACT

The present invention provides a system for measuring instantaneous inflow rate of liquid, comprising: a receptacle, comprising an opening at a top side, a nozzle at a bottom and/or multiple holes on the side section of said receptacle configured to receive the inflow of liquid from said top opening, and simultaneously release said liquid through said nozzles; a sensing device, configured to sense the level of liquid within the receptacle and produce signals indicative of the level of liquid in the receptacle; and a processor, configured to receive said signals, calculate the level of liquid in the receptacle according to said signals; and analyze said calculations, to obtain the instantaneous inflow rate of liquid.

10 Claims, 12 Drawing Sheets

(51) Int. Cl.
  *G01F 23/24* (2006.01)
  *G01F 23/26* (2022.01)
(52) U.S. Cl.
  CPC .... *G01F 23/261* (2013.01); *A61B 2562/0214* (2013.01); *A61B 2562/0219* (2013.01); *A61B 2562/164* (2013.01)
(58) Field of Classification Search
  CPC .... A61B 2562/0214; A61B 2562/0219; A61B 2562/164; G01F 23/24; G01F 23/241; G01F 23/242; G01F 23/26; G01F 23/261
  See application file for complete search history.

(56) References Cited

U.S. PATENT DOCUMENTS

| | | |
|---|---|---|
| 3,642,171 A | 2/1972 | Ernst |
| 3,919,455 A | 11/1975 | Sigdell et al. |
| 4,051,431 A * | 9/1977 | Wurster ............ G01F 1/00 73/304 C |
| 4,100,802 A | 7/1978 | Layton |
| 4,137,573 A | 2/1979 | Kroeger |
| 4,187,722 A | 2/1980 | Layton |
| 4,200,112 A | 4/1980 | McWhorter |
| 4,203,169 A | 5/1980 | Dale |
| 4,241,017 A | 12/1980 | Balistreri et al. |
| RE30,607 E | 5/1981 | Manschot et al. |
| 4,287,775 A | 9/1981 | Hutton |
| 4,301,813 A | 11/1981 | Merry et al. |
| 4,343,316 A | 8/1982 | Jespersen |
| 4,554,687 A | 11/1985 | Carter et al. |
| 4,589,280 A | 5/1986 | Carter |
| 4,590,805 A | 5/1986 | Baird et al. |
| 4,599,895 A | 7/1986 | Wiseman |
| 4,656,873 A | 4/1987 | Stewart |
| 4,658,834 A | 4/1987 | Blankenship et al. |
| 4,683,748 A | 8/1987 | Carter |
| 4,753,249 A | 6/1988 | Muller |
| 4,793,190 A | 12/1988 | Chang |
| 4,860,767 A | 8/1989 | Maekawa |
| 4,901,736 A | 2/1990 | Huang |
| 4,962,550 A | 10/1990 | Ikenaga et al. |
| 4,982,741 A | 1/1991 | Saito et al. |
| 5,062,304 A | 11/1991 | Van Buskirk et al. |
| 5,078,012 A | 1/1992 | Ding et al. |
| 5,119,675 A | 6/1992 | Mohiuddin |
| 5,263,370 A | 11/1993 | Murata et al. |
| 5,487,393 A | 1/1996 | Haswell et al. |
| 5,638,174 A | 6/1997 | Henderson |
| 5,807,278 A | 9/1998 | McRae et al. |
| 5,823,972 A | 10/1998 | McRae |
| 6,079,280 A | 6/2000 | Miller et al. |
| 6,212,698 B1 | 4/2001 | Stingley et al. |
| 6,358,477 B1 | 3/2002 | Webb et al. |
| 6,479,727 B1 | 11/2002 | Roe |
| 6,582,379 B1 | 6/2003 | Stisen |
| 6,640,649 B1 | 11/2003 | Paz et al. |
| 7,416,542 B2 | 8/2008 | Aundal |
| 7,607,362 B1 | 10/2009 | Brost |
| 7,739,907 B2 * | 6/2010 | Boiarski ............ A61B 10/007 73/304 C |
| 7,811,237 B2 | 10/2010 | Brohan et al. |
| 8,337,476 B2 | 12/2012 | Greenwald et al. |
| 8,567,258 B2 | 10/2013 | Belotserkovsky |
| 8,986,613 B2 | 3/2015 | Cohen |
| 9,155,525 B2 | 10/2015 | Lipinsky et al. |
| 9,592,034 B2 | 3/2017 | Hall et al. |
| 10,030,782 B2 | 7/2018 | Cochart et al. |
| 10,130,293 B2 | 11/2018 | Hidas |
| 10,182,747 B2 | 1/2019 | Charlez et al. |
| 10,219,733 B2 | 3/2019 | Shimokawa et al. |
| 10,238,314 B2 | 3/2019 | Connolly et al. |
| D873,995 S | 1/2020 | Laing et al. |
| 10,987,044 B2 | 4/2021 | Sageder et al. |
| D919,798 S | 5/2021 | Laing et al. |
| D920,502 S | 5/2021 | Laing et al. |
| D932,632 S | 10/2021 | Laing et al. |
| D932,633 S | 10/2021 | Laing et al. |
| D932,648 S | 10/2021 | Laing et al. |
| D933,238 S | 10/2021 | Laing et al. |
| D933,239 S | 10/2021 | Laing et al. |
| D933,240 S | 10/2021 | Laing et al. |
| D933,241 S | 10/2021 | Laing et al. |
| 11,369,298 B2 | 6/2022 | Swan et al. |
| D972,719 S | 12/2022 | Bladt et al. |
| 11,534,093 B2 | 12/2022 | Laing et al. |
| D978,358 S | 2/2023 | Laing et al. |
| D979,076 S | 2/2023 | Laing et al. |
| 11,793,436 B2 | 10/2023 | Laing et al. |
| 11,925,465 B2 | 3/2024 | Laing et al. |
| 2004/0100376 A1 | 5/2004 | Lye et al. |
| 2004/0243074 A1 | 12/2004 | Mulder |
| 2005/0256428 A1 | 11/2005 | Aundal |
| 2005/0256438 A1 | 11/2005 | Lombardozzi |
| 2006/0184064 A1 | 8/2006 | Paasch et al. |
| 2007/0123778 A1 | 5/2007 | Kantorovich |
| 2007/0180928 A1 * | 8/2007 | Newton ............ A61B 5/208 600/584 |
| 2008/0312538 A1 | 12/2008 | Shahar et al. |
| 2008/0312550 A1 | 12/2008 | Nishtala et al. |
| 2009/0287170 A1 | 11/2009 | Otto |
| 2011/0265576 A1 | 11/2011 | Cha et al. |
| 2015/0157512 A1 | 6/2015 | Abir |
| 2015/0342574 A1 | 12/2015 | Hall et al. |
| 2016/0029942 A1 | 2/2016 | Paulsen et al. |
| 2016/0183803 A1 | 6/2016 | Mosli et al. |
| 2016/0220079 A1 | 8/2016 | Abir et al. |
| 2017/0013562 A1 | 1/2017 | Lim et al. |
| 2017/0059384 A1 | 3/2017 | Della-Monica |
| 2017/0105670 A1 * | 4/2017 | Holt ............ G01F 23/263 |
| 2017/0135622 A1 | 5/2017 | Shimokawa et al. |
| 2017/0138772 A1 | 5/2017 | Neilson et al. |
| 2018/0064424 A1 | 3/2018 | Ulusahin |
| 2022/0354404 A1 * | 11/2022 | Van Batavia ....... A61B 5/486 |
| 2024/0108264 A1 | 4/2024 | Sageder et al. |
| 2024/0108265 A1 | 4/2024 | Laing et al. |
| 2024/0172981 A1 | 5/2024 | Laing et al. |

FOREIGN PATENT DOCUMENTS

| | | |
|---|---|---|
| DE | 2330033 A1 | 1/1975 |
| DE | 3007855 A1 | 9/1981 |
| EP | 1906726 B1 | 8/2019 |
| FI | 90593 C | 2/1994 |
| IL | 66593 A | 12/1987 |
| JP | H01105098 A | 4/1989 |
| JP | H02138829 A | 5/1990 |
| JP | H09220216 A | 8/1997 |
| JP | 09248289 A * | 9/1997 |
| JP | H09248289 A | 9/1997 |
| JP | 5162470 B2 | 3/2013 |
| WO | WO 2000/065313 A1 | 11/2000 |
| WO | WO 2009/143113 A1 | 11/2009 |
| WO | WO 2017/036952 A1 | 3/2017 |
| WO | WO 2018/036664 A1 | 3/2018 |
| WO | WO 2019/231511 A1 | 12/2019 |
| WO | WO 2019/231513 A1 | 12/2019 |
| WO | WO 2019/231514 A1 | 12/2019 |
| WO | WO 2020/222112 A1 | 11/2020 |
| WO | WO 2022/180239 A1 | 9/2022 |
| WO | WO 2023/023151 A1 | 2/2023 |

OTHER PUBLICATIONS

Chande P. K. et al., Expert based uroflow metering system', Proceedings IECON '91 1991 International Conference on Industrial Electronics, Control and Instrumentation, Kobe, Japan, 1991, pp. 1521-1524 vol. 2, doi: 10.1109/IECON.1991.239110. Abstract; Figure 1; pp. 1521-1522.

* cited by examiner

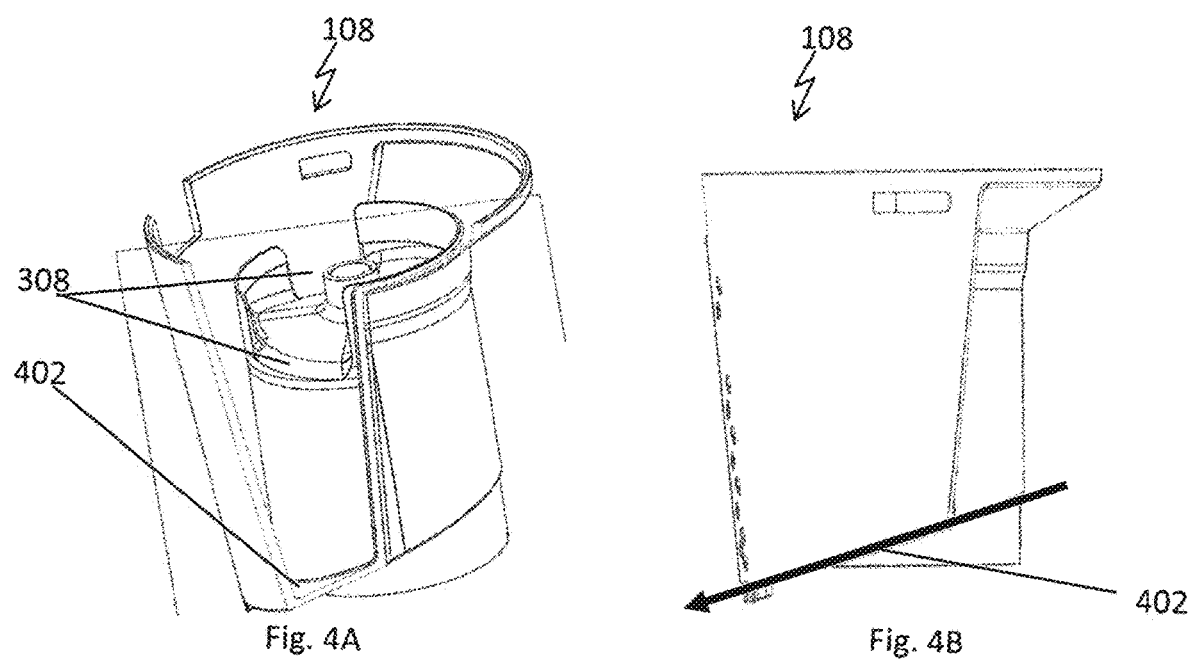

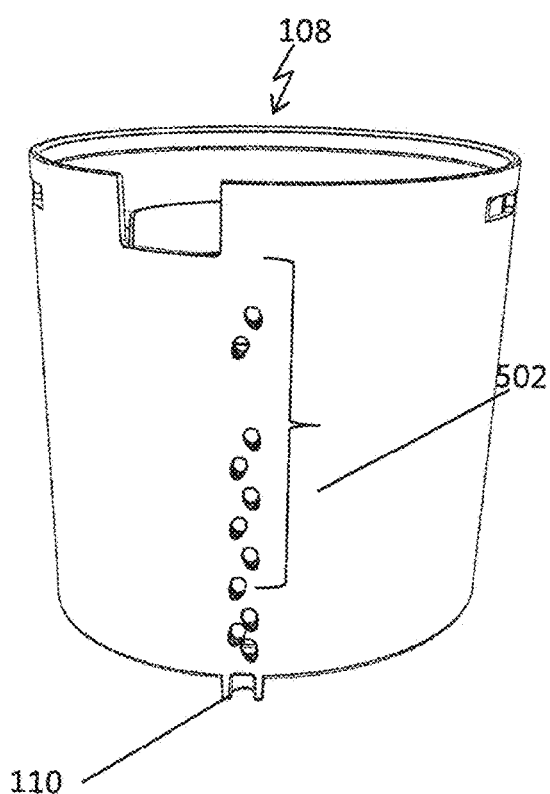
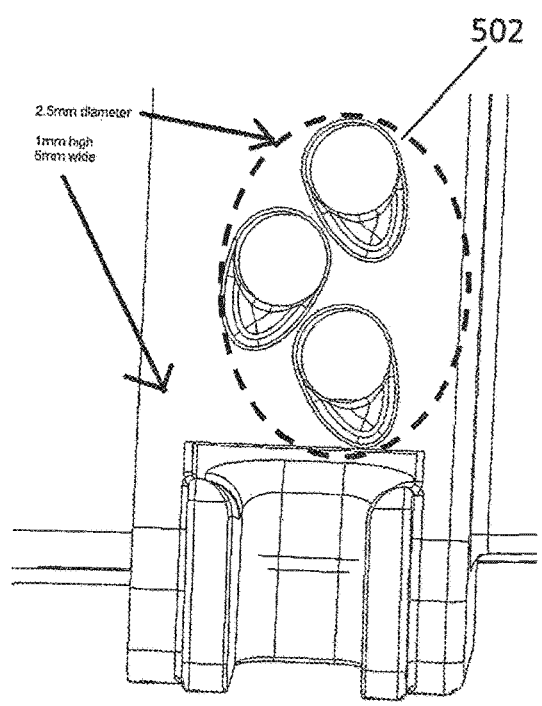
Fig. 5C
Fig. 5D

METHOD AND A SYSTEM FOR MEASURING INSTANTANEOUS INFLOW RATE OF URINE

FIELD OF THE INVENTION

The presented invention generally relates to the field of medical devices, and more specifically to methods of urine flow measurement and analysis.

DISCUSSION OF RELATED ART

Uroflowmetry is the measurement of urine flow. For humans, urine voiding events have a flow-rate in the range of 5 to 50 ml/second. Typical flow rates for healthy adults are in the range of 15 to 25 ml/sec, depending on the age and gender of the patient. Abnormal urine flow may have patterns of tower, plateau, interrupted or staccato and/or may be less than 10 ml/sec. Such deviations from normal urine flow may be indicative of various medical conditions, such as urinary tract obstruction, overactive urine bladder or underactive urine bladder.

In order for urine flow meters to be effective as physician support systems, they must be able to relate to the full dynamic range of expected urinary flow. They must also be able to detect the commencement of low flow rate periods and individual droplets, to indicate an interrupted or restricted flow.

Urine flow meters should mitigate the inertia effects of urine hitting the device at various angles, or falling from different heights, and prevent high velocity urine from flowing directly onto the measurement device and disrupting flow measurement.

SUMMARY OF THE INVENTION

The present invention discloses a system for measuring instantaneous inflow rate of liquid, such as water or urine, comprising:
- a receptacle, comprising an opening at a top side and a nozzle on a lateral side, configured to receive the inflow of liquid from said top opening, and simultaneously release said liquid through said nozzle;
- a sensing device, configured to sense the level of liquid within the receptacle and produce signals indicative of the level of liquid in the receptacle; and
- a processor, configured to receive said signals, calculate the level of liquid in the receptacle according to said signals; and analyze said calculations, to obtain the instantaneous inflow rate of liquid.

According to some embodiments of the present invention the sensing device comprises at least one electrode, placed along an inner side of a lateral wall of the receptacle, such that an increasingly longer portion of the at least one electrode is covered with liquid as liquid level (H) rises, wherein the sensing device is configured to sense specific physical qualities including at least one of resistance, or capacitance of the liquid as a function of the portion of the electrode that is covered by liquid, wherein the sensing device produces signals that are indicative to the sensed physical qualities, and propagate the signals to the processor According to some embodiments of the present invention the sensing device is a resistive sensor which comprises three electrodes, wherein the sensing device is configured to sense the resistance of liquid covering said three electrodes and produce signals that are indicative of the liquid level H.

According to some embodiments of the present invention the sensing device comprising three electrodes which create an electric circuit:
- a first electrode comprises insulated and uninsulated portions, wherein the insulated part is placed along the inner side of the receptacle wall and uninsulated part on the bottom of the receptacle.
- a second electrode which is completely uninsulated, that runs along the inner side of the receptacle.
- wherein an excitation electric voltage signal (Vin) is applied to the second electrode a third electrode completely uninsulated, running along the inner side of the receptacle serving as a common reference (GND) to the first and second electrodes, wherein the electronic circuit is configured to sense an output voltage (Vout) between the third and the second electrodes to produce signals that are indicative of Vout to the processor.

According to some embodiments of the present invention the processor is configured to calculate the inflow Qin by applying the steps of:
- calculate H according to the known Vin and said signals that are indicative of Vout, via;
- calculate dH/dt by differentiating between H values pertaining to consequent samples of Vout; and
- calculate A(H) according to H, and the known geometry of the receptacle;

According to some embodiments of the present invention the level sensing operation is based on measuring the relative conductance between two electrodes and a series of multiple receiving pads electrodes that are spaced apart vertically.

According to some embodiments of the present invention the value of Qout as a function of H is empirically measured during a calibration process, to produce a lookup table, associating a given liquid level H with a momentary value of liquid outflow Qout.

According to some embodiments of the present invention the value of Qout as a function of H is dependent upon structural parameters of the receptacle and the outlet section, therefore computable according to parameters of the receptacle's dimensions.

According to some embodiments of the present invention the system of claim 1 wherein the outlet nozzle is between 4-7 mm, thus enhancing the linearity of Qout as a function of H throughout the entire expected flow range.

According to some embodiments of the present invention the multiple holes on the side section of said receptacle are configured, for enhancing the linearity of Qout as a function of H throughout the entire flow range.

According to some embodiments of the present invention the systems further comprising an accelerometer which measures the tilt of the system to compensate for deviation liquid level measurement.

According to some embodiments of the present invention the respectable is comprised of: an inner element having a cylindrically-shaped part and a dome-shaped upper part, wherein the dome-shaped upper part absorbs the kinetic energy of the fluid flowing into open receptacle, eliminating the effects of urine disposal height and orientation, and enabling the apparatus to measure urine flow as the momentary quantity of disposed urine;

According to some embodiments of the present invention the upper dome comprises a plurality of openings along its circumferential side walls and similarly, inner element comprises a plurality of openings along its circumferential side wall, hence the dome-shaped upper part spreads the flow evenly across the inner walls of the open receptacle.

BRIEF DESCRIPTION OF THE DRAWINGS

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 4A illustrates the inner structure of an embodiment of the open receptacle;

FIG. 4B illustrates an isometric side view of an embodiment of the open receptacle;

FIG. 5C illustrates a front view of an embodiment of the open receptacle with the outlet nozzle and discharge holes;

FIG. 5D is a magnified view of an embodiment of the nozzle and the discharge holes;

DETAILED DESCRIPTION

The present invention discloses a system and a method for easy, accurate and reproducible measurement of an instantaneous inflow rate (Qin) and volume of liquid such as water or urine into a receptacle.

In the case of urine inflow measurement, the system is configured to:
- Be fitted within standard toilet pans, requiring very limited height and volume;
- Be evacuated from urine through normal operation, and not require manual evacuation of a receptacle (flow through); and
- Measure inflow rates from 5 to 50 ml/sec, and practically unlimited volume, thus covering the entire scope of human biological variations.

Figure 1:
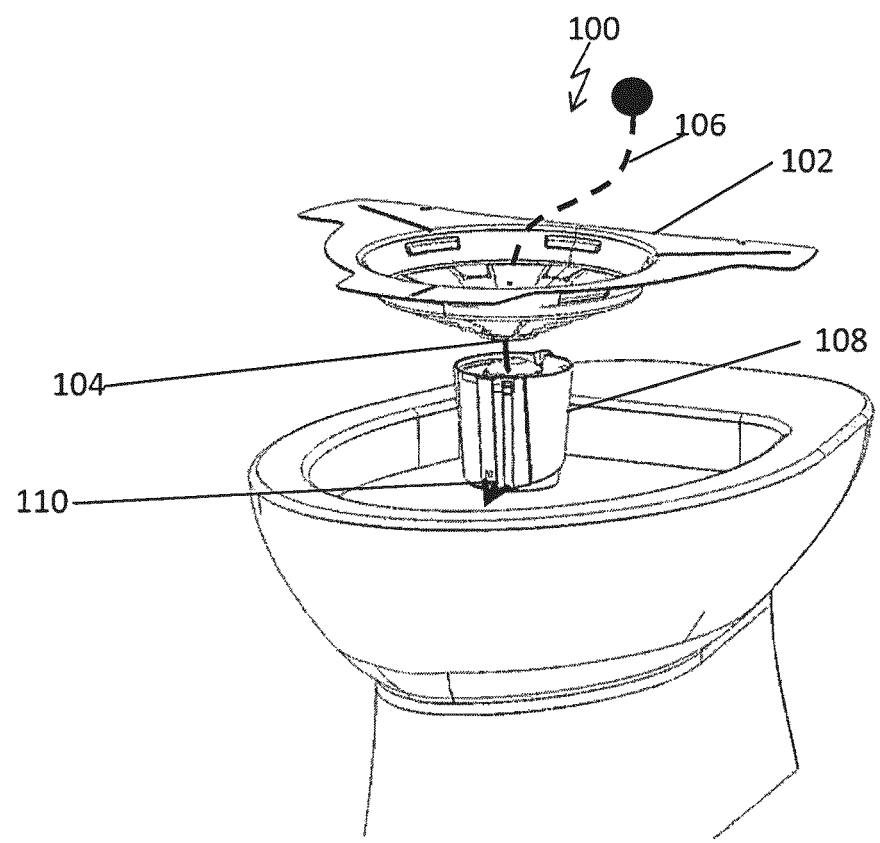
FIG. 1 presents an elevated, isometric exploded view of an embodiment of the system configured to be placed over a toilet bowl or seat.

FIG. 1 presents an elevated, isometric exploded view of the system 100, as it is configured to be placed over a toilet bowl or seat, according to some embodiments of the present invention. The system 100 comprises:

- a receptacle bowl 102 configured to be placed over a toilet bowl or seat, and direct fluid through a single point of exit 104;
- incoming fluid 106 from the receptacle bowl 102 allowing the fluid 106 to proceed towards an open receptacle 108.
- open receptacle 108 configured to receive the inflow of liquid from an opening at its top side, and simultaneously release the liquid through an outlet nozzle 110 at the bottom section of said open receptacle 108, for instance, on a lateral side towards the toilet drain;
- a sensing device (not shown), configured to sense the Level of Liquid (H) within the receptacle 108 and produce signals indicative of H; and
- a processor (not shown), configured to produce the calculated instantaneous inflow rate (Qin) of fluid 106 from the signals.

In accordance with some embodiments of the present invention, outlet nozzle 110 may be an outlet slit, a strainer and the like.

Figure 2:
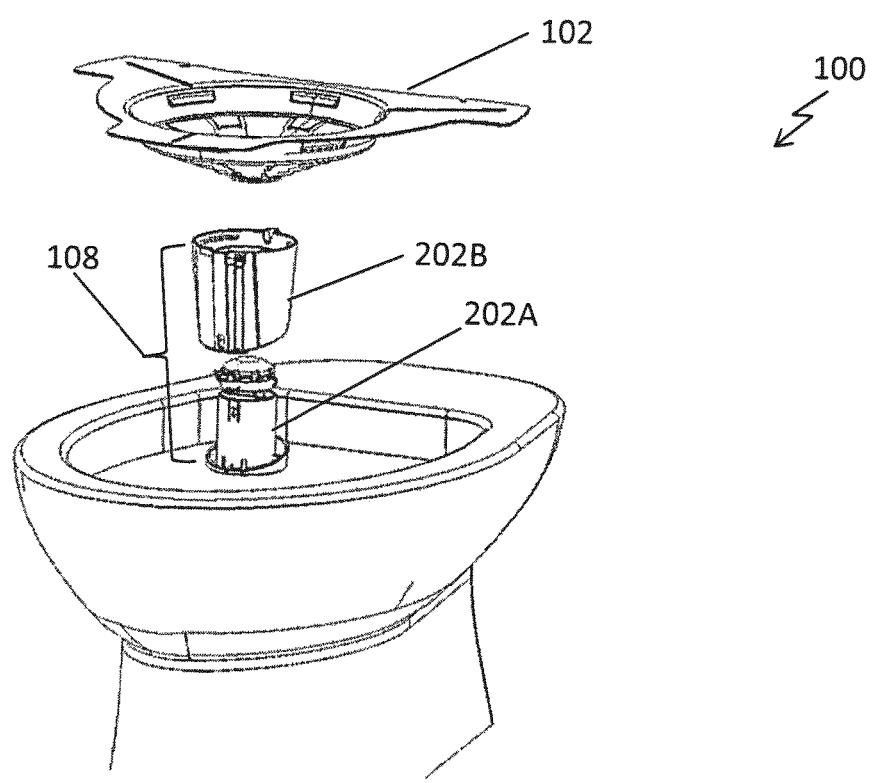
FIG. 2 presents an elevated, isometric exploded view of an embodiment of the system installed over a toilet bowl or seat.

FIG. 2 presents an elevated, isometric exploded view of system 100, as it is installed over a toilet bowl or seat, according to some embodiments. Seen in the figure, open receptacle 108 comprises an inner element 202A and an outer element 202B the roles of which are described below. In these embodiments, open receptacle 108 is configured to directly attach to the receptacle bowl 102.

Figure 3A:
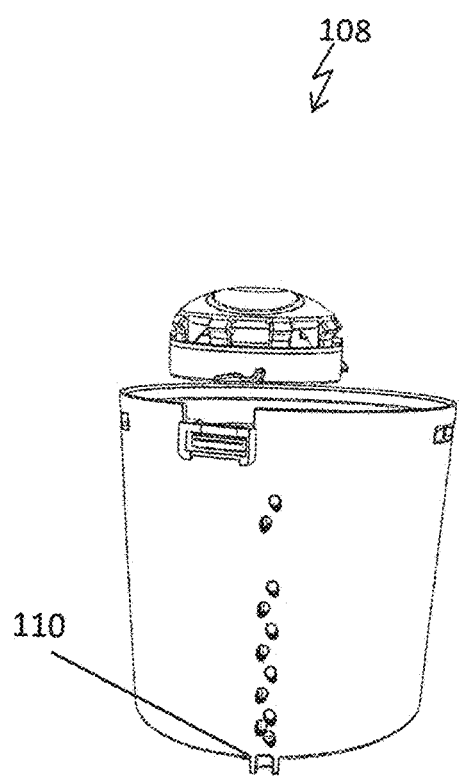
FIG. 3A illustrates a side view of an embodiment of an open receptacle showing an outlet nozzle.
Figure 3B:
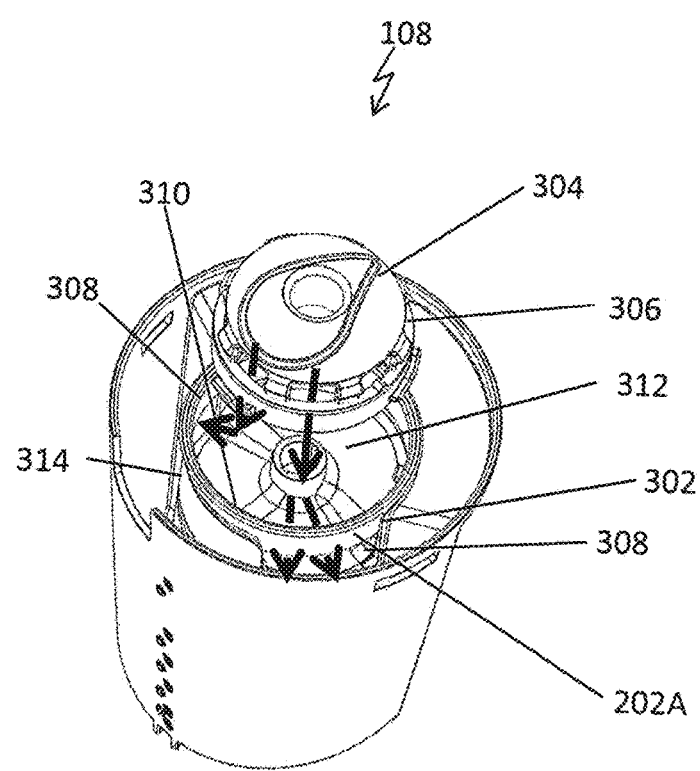
FIG. 3B illustrates a perspective view of an embodiment of the open receptacle.

FIG. 3A illustrates a side view of open receptacle 108 showing outlet nozzle 110, and FIG. 3B illustrates a perspective view of open receptacle 108.

Seen in FIG. 3B, inner element 202A. A cylindrically-shaped part 302 and a dome-shaped upper part 304. The upper part 304 has discharge holes on the lateral side, this configuration enables more consistence and linear outflow The dome-shaped upper part 304 serves multiple purposes:
- the dome-shaped upper part 304 absorbs the kinetic energy of the fluid flowing into open receptacle 108, eliminating the effects of urine disposal height and orientation, and enabling the apparatus to measure urine flow as the momentary quantity of disposed urine.
- the existence of bubbles in the inspected urine has a potentially disruptive effect on the accuracy of the fluid flow rate measurement, as bubbles acquire volume within the receptacle 108. The dome-shaped upper part 304 utilizes the fluid tension produced when the fluid contacts the dome to extract air bubbles from the fluid.
- turbulence of fluid flowing into the receptacle also has a potentially disruptive effect on the accuracy of the fluid flow rate measurement. The dome-shaped upper part 304 reduces turbulence by receiving a turbulence flow and delivering a laminal flow through the dome's walls, into the open receptacle 108.

The dome-shaped upper part 304 spreads the flow evenly across the inner walls of the open receptacle 108. As seen in the figure, dome-shaped upper part 304 is not sealed but rather comprises a plurality of openings 306 along its circumferential side walls [308]. Similarly, inner element 202A comprises a plurality of openings 308 along its circumferential side wall 310. Such openings elaborate the flow path of liquid as indicated by the arrows through the system. As the liquid hits the dome-shaped upper part 304, it flows and enters through openings 306 into the antechamber 312 underneath dome-shaped upper part 304. The liquid flows through the semi-circular openings 308 at the cylindrically-shaped side wall 310 into the internal section 314 of open receptacle 108.

FIG. 4A illustrates the inner structure of open receptacle 108 in accordance with some embodiments of the present invention. Seen in the figure is a plurality of semi-circular openings 308 through which liquid is flowing into the internal section 402 of open receptacle 108.

In accordance with some embodiments of the present invention, open receptacle 108 is designed to enable flow rate measurements of the liquid flowing therein, based on which the volume flow and emptying time can then be calculated and extrapolated. FIG. 4B illustrates an isometric side view of open receptacle 108. Seen in the figure, open receptacle 108 is designed in a way that at the end of a flow test, it must be self-emptied, thus, as seen in the figure, open receptacle 108 comprises a sloping floor 402 to allow proper drainage.

In accordance with some embodiments of the present invention, open receptacle 108 is designed to fit within every toilet depth and therefore may be as short as 70 mm.

In accordance with some embodiments of the present invention, open receptacle 108 has separation of heights for every change in flow rate, as instantaneous flow changes (for example, distinct between 20 mlps flow rate and 19 mlps flow rate).

Figure 5A:
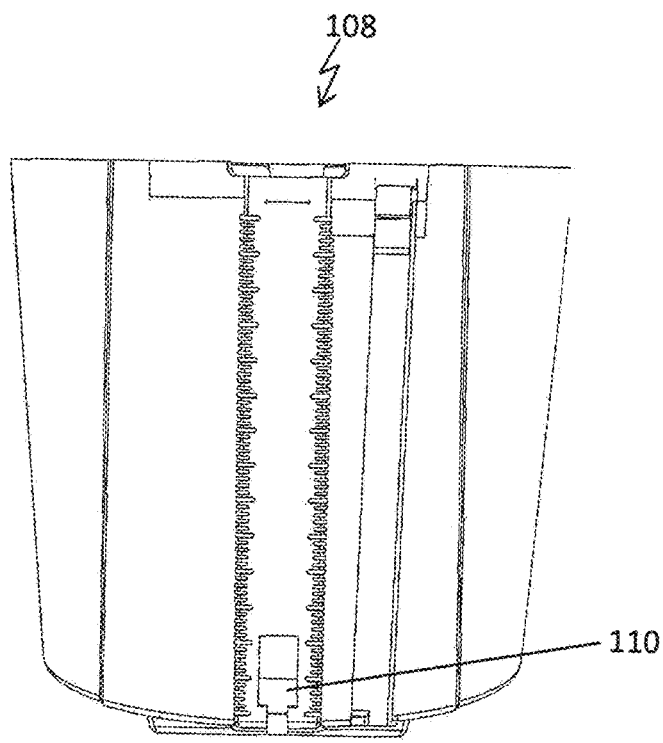
FIG. 5A illustrates a front view of an embodiment of the open receptacle.

In accordance with some embodiments of the present invention as seen in FIG. 5A, open receptacle 108 is designed to have an optimal orifice outlet size or multiple orifices outlets (as seen FIG. 5C) of discharge holes to allow a linear flow rate separation as instantaneous flow rate is changing.

In accordance with some embodiments, an aim of the present invention is to have residual urine in open receptacle 108 while urine flows in and out of outlet nozzle 110. The discharge flowrate via outlet nozzle 110 is changing as the residual in the container is changing. Therefore, in accordance with some embodiments of the present invention, the size of nozzle 110 and the dimensions of open receptacle 108 are optimized so that changes in the flowrate of urine entering outlet nozzle 110 may be reflected in changes in both the residual urine height within open receptacle 108 and the discharge rate. For instance, in case the outlet nozzle 110 is not optimal, the residual urine height within open receptacle 108 is same for flow rates of 30 mlps and 33 mlps. The reason for this is that gravitational pressure presses down on the residual urine and if outlet nozzle 110 is limited, there may be a scenario where the discharge rate out of outlet nozzle 110 is greater but the residual urine height within open receptacle 108 remains the same. Such scenario may result in the inability to separate flow rates.

In accordance with some embodiments of the present invention, an optimal design of open receptacle 108, i.e., a design which enables the separation of flow rates is illustrated below in FIGS. 5C & D.

Figure 5B:
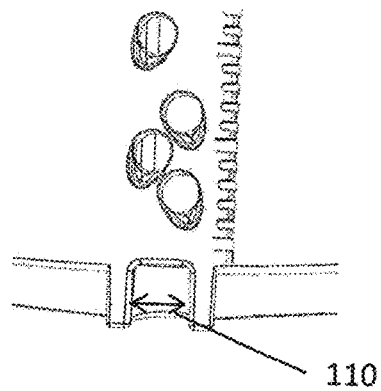
FIG. 5B is a magnified view of an embodiment of an outlet nozzle.

FIG. 5A illustrates a front view of open receptacle 108, and FIG. 5B is a magnified view of an outlet nozzle 110. Seen in the figure, outlet nozzle 110 may be relatively narrow to allow for measurements of relatively low flow rates. For instance, outlet nozzle 110 may be about 4-7 mm in width, and preferably 5 mm and 0.5 to 2 mm high and preferably 1 mm to allow a flow rate of about 3 mlps. Such narrow outlet section leads to relatively low flow rates which enable the sensing device to measure changes in liquid height within open receptacle 108.

FIG. 5C illustrates a front view of open receptacle 108 with outlet nozzle 110 and a series of discharge holes 502 through which liquid is draining out of open receptacle 108. Such combination of outlet nozzle 110 and multiple discharge holes 502 reflects changes in the flowrate of urine entering outlet nozzle 110 on both the residual urine height within open receptacle 108 and the discharge rate, i.e., producing a highly linear discharge rate.

In accordance with some embodiments of the present invention, the number of holes 502 as well as their size, shape and position in open receptacle 108 may vary for optimizing the resulting discharge rate.

FIG. 5D is a magnified view of nozzle 110 and discharge holes 502 in accordance with some embodiments of the present invention.

Figure 6:
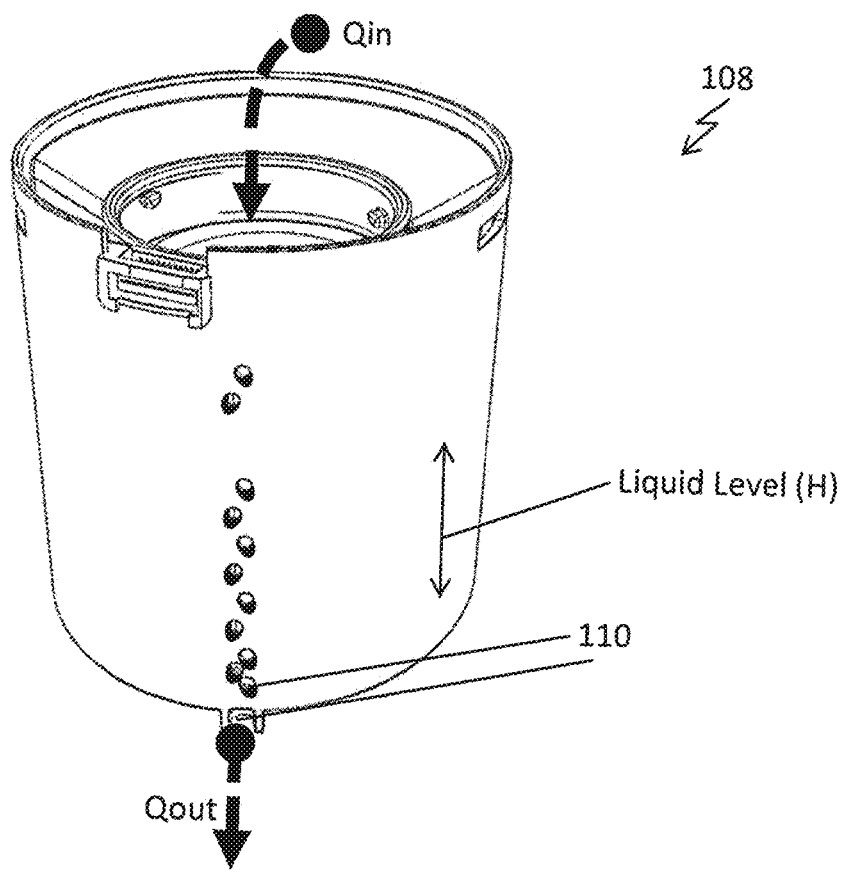
FIG. 6 presents an elevated, isometric view of an embodiment of the open receptacle.

FIG. 6 presents an elevated, isometric view of open receptacle 108, according to some embodiments of the present invention.

The evacuation of liquid via outlet nozzle 110 facilitates momentary measurement of Qin, rather than deduction of Qin from differential measurement of the volume of liquid accumulated within the receptacle.

Outlet nozzle 110 is configured to evacuate the liquid from open receptacle 108 at an outflow rate Qout, which is a single-variable function of the level of liquid within the receptacle (H). Qout is therefore directly computable from the calculated H produced by the processor. The nozzle is located at the lowest gravitational point and therefore enabling consistence and measurable height to discharge ration in addition to ensuring that a full drainage is achieved.

According to some embodiments, the value of Qout as a function of H is empirically measured during a calibration process, so as to produce a lookup table, associating a given liquid level H with a momentary value of liquid outflow Qout.

According to some embodiments, the value of Qout as a function of H is dependent upon structural parameters of the receptacle and the outlet section (e.g. inclination of receptacle walls, width of the outlet section, etc.), and is therefore computable according to parameters of the receptacle's dimensions.

According to some embodiments, outlet nozzle 110 is relatively narrow, about 2 mm, thus enhancing the linearity of Qout as a function of H throughout the entire expected flow range, i.e., between 5 and 50 ml per second.

The evacuation of liquid via outlet nozzle 110 provides the following benefits to the present invention:
Liquid is not stored within the receptacle at any stage. This facilitates a reduced form factor, resulting in reduced receptacle volume and sensor size. This is particularly advantageous when the system is utilized for measuring inflow of urine, enabling the installation of the system within a toilet bowl.
It is not necessary to clear or clean the receptacle at the end of the measurement. This is also particularly advantageous when measuring inflow of urine.

According to some embodiments of the present invention, the sensing device comprises at least one electrode, placed along an inner side of a lateral wall of the receptacle, such that an increasingly longer portion of the electrode(s) is covered with liquid as H rises. The sensing devices are configured to sense specific physical qualities (e.g. resistance, capacitance) of the liquid as a function of the portion of the electrode that is covered by liquid. The sensing device produces signals that are indicative to the sensed physical qualities, and propagate the signals to the processor. The processor is configured to calculate H according to said signals, and analyze the calculations to obtain the instantaneous inflow rate of liquid (Qin) through the following formula:

$$Qin = \left(\frac{dH}{dt} * A(H)\right) - Qout \qquad [\text{eq. 1}]$$

Wherein:
Qin is the instantaneous inflow rate through the opening at the receptacle's top side
Qout is the instantaneous outflow rate from the receptacle via outlet nozzle 110 at the specified H;
dH/dt is the time-derivative of H (Liquid level in the receptacle); and
A(H) is the surface area of liquid at liquid level H (a known function of the receptacle's geometry).

The function and different embodiments of the sensing devices are further elaborated below.

Figure 7:
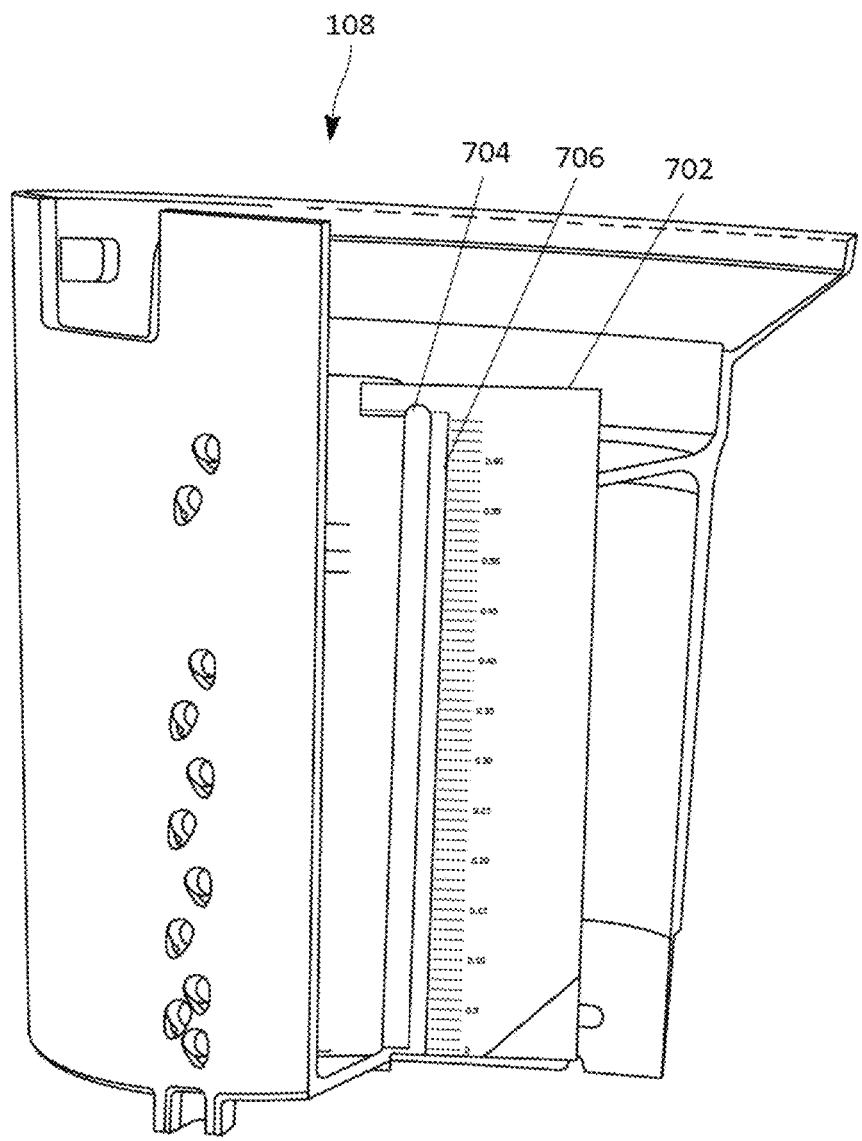
FIGS. 7 and 8 illustrate a side view and a perspective top view, respectively, of an embodiment of the open receptacle with a sensing device.
Figure 8:
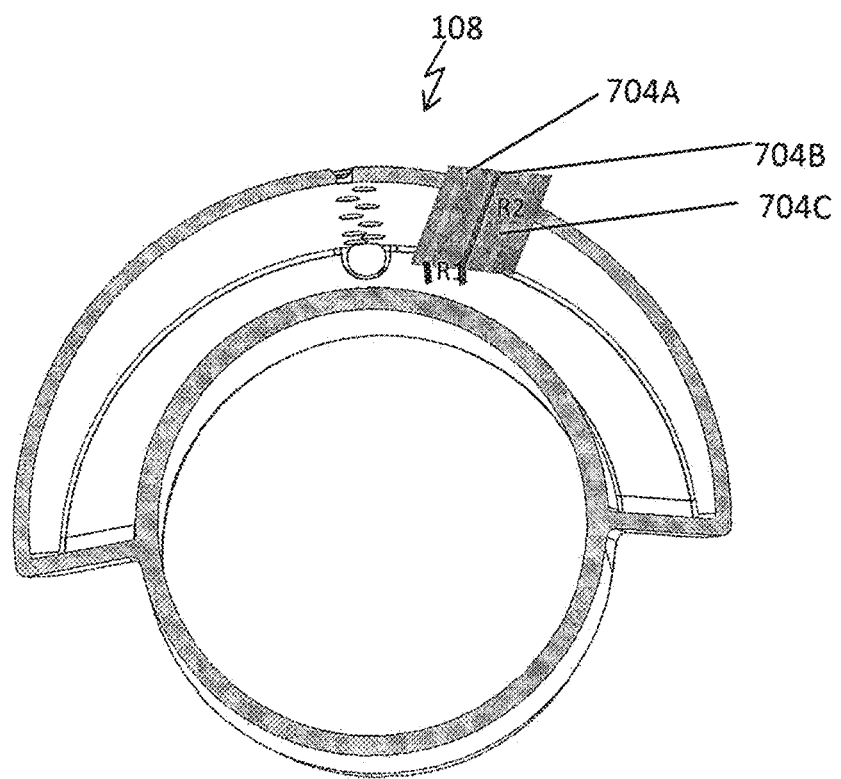

FIGS. 7&8 illustrate a side view and a perspective top view of the open receptacle 108 with sensing device 702, according to some embodiments of the present invention. As seen in FIG. 7, the sensing device 702 is a resistive sensor comprising electrodes 704 A-C and pads 706. The sensing device 702 is configured to sense the resistance of liquid covering said electrodes 704A-C and pads 706 and produce signals that are indicative of the liquid level H. The signals, at each pad location, are devoid of the effect of variable resistivity between measured liquids, e.g., due to varying concentrations of Total Dissolved Solids (TDS).

As seen in FIG. 8, sensing device 702 comprising 3 electrodes, Electrode 704A, Electrode 704B, and Electrode 704C.

Electrode 704A comprises insulated and uninsulated parts (may be implemented in different configurations). The electrode is placed along the inner side of the receptacle wall (insulated) and the bottom of the receptacle (uninsulated).

Electrode 704B is completely uninsulated. An excitation electric voltage signal (Vin) is applied to the top, insulated portion of electrode 704B.

Electrode 704C is also completely uninsulated. It runs along the inner side of the receptacle 108, serving as a common reference (GND) to electrodes 704A and 704B.

The three electrodes create an electronic circuit that is configured to sense an output voltage (Vout) between electrodes 704A and 704B (R1), and between 704B and 704C (R2) produces signals that are indicative of Vout to the processor.

As soon as liquid flows into the receptacle, the resistance R1 between electrodes 704A and 704B is reduced due to conduction through the liquid at the base of the receptacle.

The sensing device is configured to sense the electric capacitance between the respective pairs of electrodes, and produce signals that are indicative of the liquid level H. The said signals are devoid of the effect of variable capacitance between different measurements that may arise, for example, from variations in the permittivity (dielectric constant) of the measured liquids or different environmental conditions in which the measurements have taken place (e.g. temperature).

Figure 9:
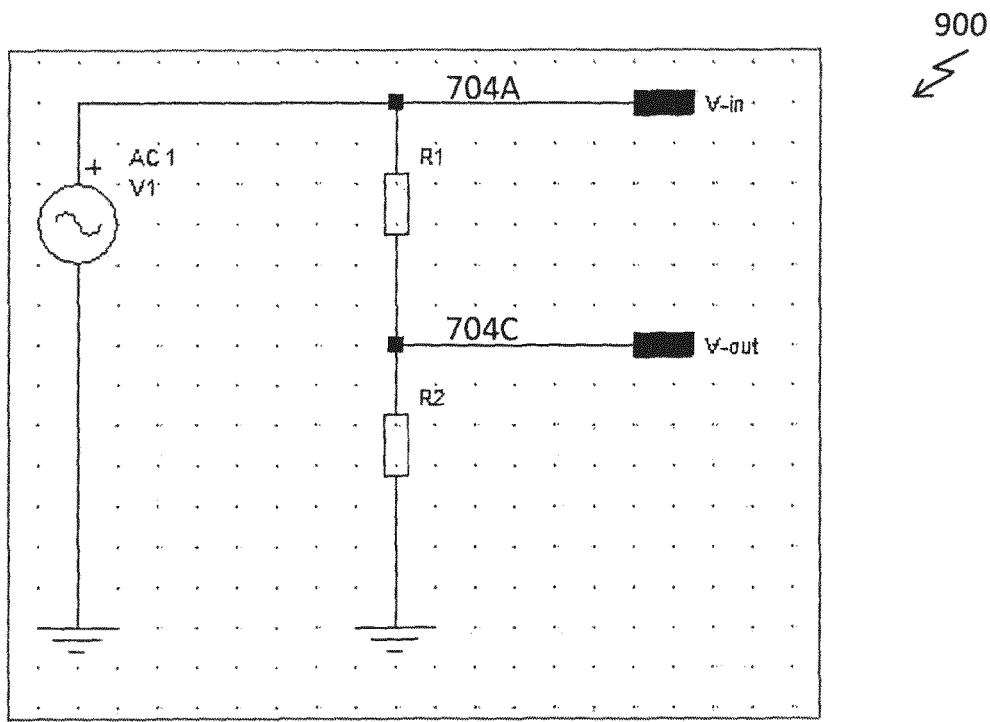
FIG. 9 illustrates an embodiment of an electric circuit equivalent to the constellation of electrodes depicted in FIG. 8.
Figure 10:
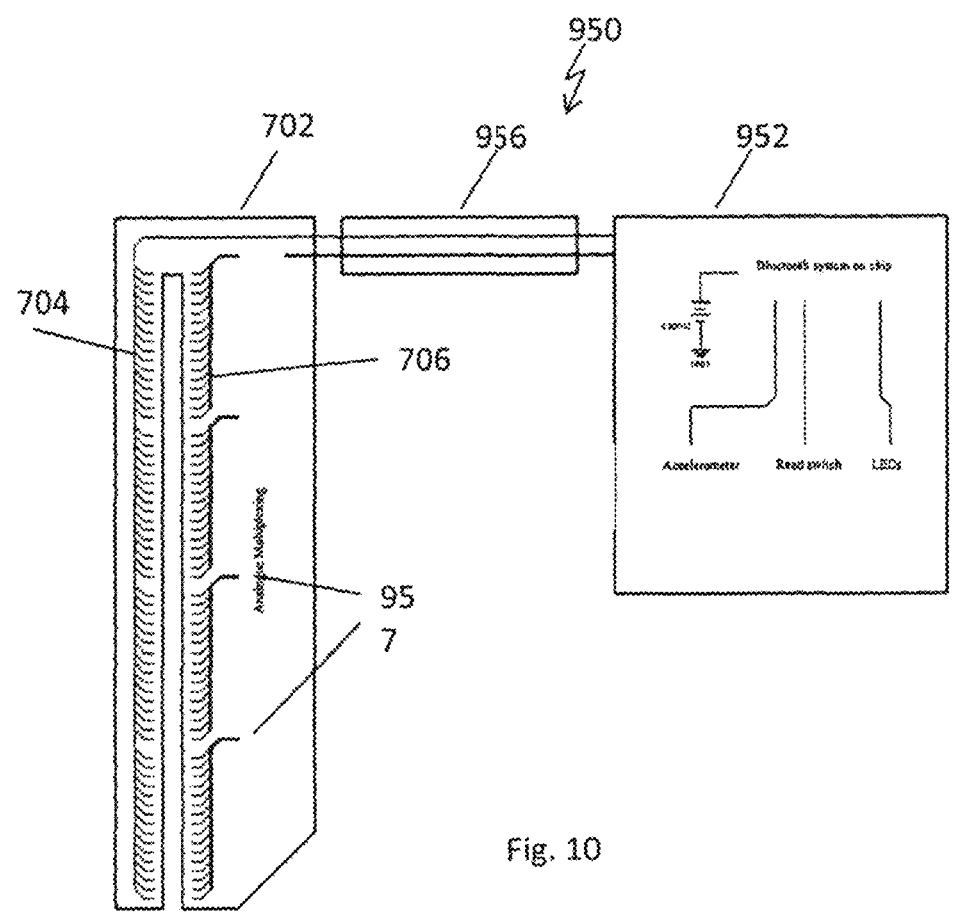
FIG. 10 illustrates an embodiment of the system hardware.
Figure 11:
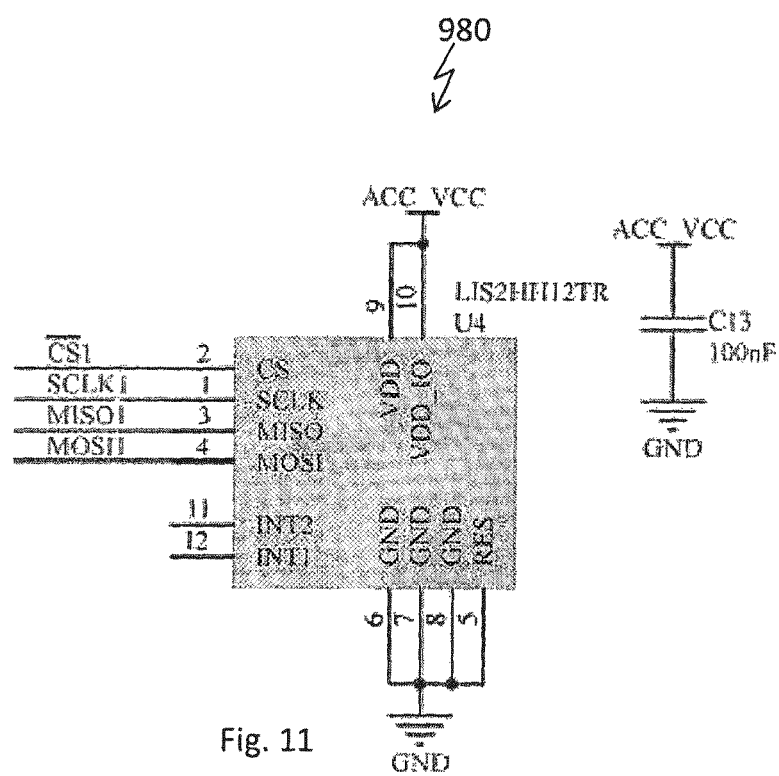

FIG. 9 illustrates an electric circuit 900 that is equivalent to the constellation of electrodes 704A-C depicted in FIG. 8, for explaining the behavior of the resistance throughout the process of liquid level change.

An excitation electric voltage signal (Vin) is applied to electrode 704B.

The electronic circuit is configured to sense an output voltage (Vout) between electrodes 704B and 704C.

As soon as liquid flows into the receptacle, the resistance R1 between electrodes 704A and 704B is reduced due to conduction through the liquid at the base of the receptacle and therefore, R1 remains constant throughout the measurement, and is not affected by the liquid level H.

As the level of liquid H increases, the resistance R2 between electrodes 704 B and C is proportionally reduced due to conduction through the liquid.

The liquid level H can therefore be expressed as $$H = K\left(\frac{Vin}{Vout} - 1\right) \qquad [\text{eq. 2}]$$

wherein K is a constant which may be empirically measured during a stage of calibration. Note that the above expression is devoid of resistance or resistivity factors, and is therefore indifferent to the conductivity of the liquid.

According to some embodiments, the processor is configured to calculate the inflow Qin by applying the steps of:
calculate H according to the known Vin and said signals that are indicative of Vout, via [eq. 2];
calculate dH/dt by differentiating between H values pertaining to consequent samples of Vout;
calculate A(H) according to H, and the known geometry of the receptacle;
calculate Qout according to said lookup table or known function of Qout(H); and
obtain Qin according to above, via [eq. 1].

The invention claimed is:

1. A system for measuring inflow rate of liquid comprising:
a receptacle comprising a top portion, a bottom portion, an opening arranged at the top portion, a nozzle arranged at the bottom portion, an inner element comprising an at least partially cylindrical-shaped side wall and a plurality of openings arranged along a perimeter of the at least partially cylindrical-shaped side wall, and a dome-shaped part comprising a side wall and a plurality of openings arranged along a perimeter of the side wall of the dome-shaped part, wherein the receptacle is configured to allow a liquid to flow through the plurality of openings of the dome-shaped part and the plurality of openings of the inner element into an interior of the receptacle and out of said interior through said nozzle;
a sensing device configured to generate one or more signals indicative of a level of the liquid in the interior of the receptacle; and
a processor configured to receive said one or more signals and determine an inflow rate of the liquid based on said one or more signals.

2. The system of claim 1 wherein the nozzle comprises a width that is between 4-7 mm.

3. The system of claim 1 wherein the receptacle further comprises a plurality holes on an outer wall said receptacle.

4. The system of claim 1 further comprising an accelerometer for measuring tilt of the system.

5. The system of claim 1 wherein the dome-shaped part is removable from the at least partially cylindrical-shaped side wall.

6. The system of claim 1 further comprising a bowl configured to be placed over a toilet, the bowl further configured to attach to the receptacle and guide said liquid towards the dome-shaped part of the receptacle.

7. The system of claim 1 wherein the sensing device comprises at least one electrode, and wherein said one or more signals are indicative of at least one of resistance and capacitance of the liquid.

8. The system of claim 1 wherein said nozzle is arranged at a perimeter of an outer wall of the receptacle.

9. The system of claim 1 wherein the receptacle further comprises an outer wall, and wherein said interior is defined between at least a portion of said outer wall and at least a portion of said inner element.

10. The system of claim 1 wherein the receptacle further comprises a sloping floor at the bottom portion.

* * * * *